United States Patent
Mizuno et al.

(10) Patent No.: US 10,143,762 B2
(45) Date of Patent: Dec. 4, 2018

(54) ARTICULAR CARTILAGE IMAGING COMPOSITION

(71) Applicants: Mercury Asset Management Co., Ltd., Osaka (JP); Yasunori Fujiwara, Tokyo (JP)

(72) Inventors: Shuichi Mizuno, Shizuoka (JP); Nobuaki Kawaguchi, Tokyo (JP); Akihiro Tsuchiya, Chiba (JP); Yoshinobu Manome, Kanagawa (JP)

(73) Assignee: Mercury Assel Management Co., Ltd., Osaka (JP)

( * ) Notice: Subject to any disclaimer, the term of this patent is extended or adjusted under 35 U.S.C. 154(b) by 211 days.

(21) Appl. No.: 15/039,123

(22) PCT Filed: Dec. 8, 2014

(86) PCT No.: PCT/JP2014/082441
§ 371 (c)(1),
(2) Date: May 25, 2016

(87) PCT Pub. No.: WO2015/087839
PCT Pub. Date: Jun. 18, 2015

(65) Prior Publication Data
US 2017/0157271 A1   Jun. 8, 2017

(30) Foreign Application Priority Data
Dec. 13, 2013 (JP) .................................. 2013-257892

(51) Int. Cl.
*A61K 49/00* (2006.01)

(52) U.S. Cl.
CPC ...... *A61K 49/0034* (2013.01); *A61K 49/0002* (2013.01); *A61K 49/0056* (2013.01)

(58) Field of Classification Search
CPC ................ A61K 49/00; A61K 49/0034; A61K 49/0002; A61K 49/0056
See application file for complete search history.

(56) References Cited

U.S. PATENT DOCUMENTS

| | | |
|---|---|---|
| 2002/0034537 A1 | 3/2002 | Schulze et al. |
| 2002/0071843 A1 | 6/2002 | Li et al. |
| 2005/0282084 A1 | 12/2005 | Barr et al. |
| 2007/0014730 A1 | 1/2007 | Brief et al. |
| 2011/0002927 A1 | 1/2011 | Urech et al. |

FOREIGN PATENT DOCUMENTS

| | | |
|---|---|---|
| JP | 2004-511426 | 4/2004 |
| JP | 2004-535407 | 11/2004 |
| JP | 2008-544968 | 12/2008 |
| JP | 2009023993 | 2/2009 |
| JP | 2011-510667 | 4/2011 |
| WO | WO 2013/137302 | 9/2013 |

OTHER PUBLICATIONS

Sigma-Aldrich, Product Specification, Gadolinium chloride GdCl3 Mar. 30, 2018.*
Foy et al., Diffusion of Paramagnetically Labeled Proteins in Cartilage: Enhancement of the 1-D NMR Imaging Technique, Journal of Magnetic Resonance 148, 126-134 (2001).*
van Lent et al., Electrical charge of a protein determines penetration and localization in hyaline articular cartilage; Quantitative and autoradiographic studies on cartilage of different species, including man, Rheumatol Int (1988) 8: 145-152.*
Werner et al., Indocyanine Green-Enhanced Fluorescence Optical Imaging in Patients with Early and Very Early Arthritis, Arthritis & Rheumatism, vol. 65, No. 12, Dec. 2013, pp. 3036-3044.*
Oh et al., Intraoperative combined color and fluorescent images-based sentinel node mapping in the porcine lung: Comparison of indocyanine green with or without albumin premixing, The Journal of Thoracic and Cardiovascular Surgery, vol. 146, No. 6, published Feb. 14, 2013; p. 1509-1515.*
European Search Report dated May 16, 2017.
Moeini, M. et al.; "Decreased solute adsorption onto cracked surfaces of mechanically injured articular cartilage: towards the design of cartilage-specific functional contrast agents"; Biochim Biophys Acta, vol. 1840, No. 1, Jan. 2014 (Jan. 2014), pp. 605-614, XP0287973055.
Van Lent, L.E.M. et al.; "Electrical charge of a protein determines penetration and localization in hyaline articular cartilage"; Rheumatology, Mar. 10, 1988. (This reference was submitted with the IDS filed with this application May 25, 2016, but not correctly cited on PTO/SB/08b).
Russian Office Action dated Aug. 22, 2017 (Russian and English translation enclosed).

(Continued)

*Primary Examiner* — Michael G Hartley
*Assistant Examiner* — Nabila G Ebrahim
(74) *Attorney, Agent, or Firm* — Haug Partners LLP; William S. Frommer

(57) ABSTRACT

Provided is an articular cartilage imaging composition which can clearly distinguishably visualize a normal site and an abnormal site, i.e., a degenerative site, in articular cartilage. The articular cartilage imaging composition contains a positively charged molecule, which is labeled with a labeling molecule.

2 Claims, 4 Drawing Sheets

(56) References Cited

OTHER PUBLICATIONS

Reinhard Meier et al., "Indocyanine Green-Enhanced Imaging of Antigen-Induced Arthritis With an Integrated Optical Imaging/Radiography System", *Arthritis & Rheumatism*, vol. 62, No. 8, Aug. 2010, pp. 2322-2327.
Electrical Charge of the Antigen Determines Intaarticular Antigen Handling and Chronicity of Arthritis in Mice, van den Berg,an de Putte, Zwarts and Joosten, Department of Rheumatology, University Hospital, Nijmegen, the Netherlands, pp. 1850-1859.
Electrical charge of a protein determines penetration and localization in hyaline articular cartilage, Rheumatol Int. (1988), pp. 145-152.
International Clinical and Experimental Investigations, vol. 8, No. 4, 1988.
Biomaterials 35, pp. 538-549, Avidan as a model for charge driven transport into cartilage and drug delivery for treating early stage postraumatic osteoarthritis, Bajpayee, Wong, Bawendi, Frankand Grodzinsky.
Charge-Charge Interactions Between Articular Cartilage and Cationic Antibodies, Antigens, and Immune Complexes, Ernesto ZataraiRios and Mart Mannik, Arthritis and Rheumatism, vol. 30, No. I 1 (Nov. 1987) pp. 1265-1273.
Journal of Near Infrared Spectroscopy, vol. 20, No. 1, 2012, ISSN 09670335, Ferrari, Norris and Sowa.
JACS Communications, Aug. 25, 2009, Effect of Contrast Agent Charge on Visualization of Articular Cartilage Using ComputedTomography: Exploiting Electrostatic Interactions for Improved Sensitivity, pp. I3234I3235. Joshi, et al.
The Journal of the Japanese Orthopaedic Association, vol. 87, No. 8, Aug. 2013, A Near Infrared Fluorescent Imaging Using Indocyanine Green Intentional Nanoparticle in Rheumatoid ArthritisModel Mouses, Oonishi, Shinzo, et al.
A Research Regarding a Diffusion Phenomenon in Articular Cartilage Using Florescence Correlation Spectroscopy (FCS), Lee, Jeongik and Ushida, Kiminori, a general outline-sharing study report, pp. 73-79, Apr. 2008.
Journal of Magnetic Resonance 148, 126-134 (2001), Brent D. Foy, et al.
IPO of Singapore Search Report dated Feb. 24, 2017.
IPO of Singapore Written Opinion dated Mar. 10, 2017.
Korea PTO Notice of Preliminary Rejection.
Van Den Berg, et al., "Antigen Handling in Antigen-Induced Arthritis in Mice", American Assoc. of Pathologists, Jul. 1982.
Van Den Berg, et al., "Electrical Charge of the Antigen Determines Its Localization in the Mouse Knee Joint", Dept. of Rheumatology, Univ. Hosp., The Netherlands, Jun. 1985.
Foy, et al., "Diffusion of Paramagnetically Labeled Proteins in Cartilage: Enhancement of the 1-D NMR Imaging Technique, Dept. of Physics", Wright State Univ., OH, Sep. 2000.
Lee, et al., "Measurement of diffusion in articular cartilage using fluorescence correlation spectroscopy", BMC Biotechnology, 2011, pp. 1-10.
Ren, et al., "Albumin as a Delivery Carrier for Rheumatoid Arthritis", Nanomedicine & Nanotechnology, v. 4, iss. 4, 2013.
Frangioni, JV, "In vivo near-infrared fluorescence imaging", Curr. Opin. Chem, Biol,, Oct. 2003, 7(5): 626-34, [Abstract].

* cited by examiner

[Figure 1]
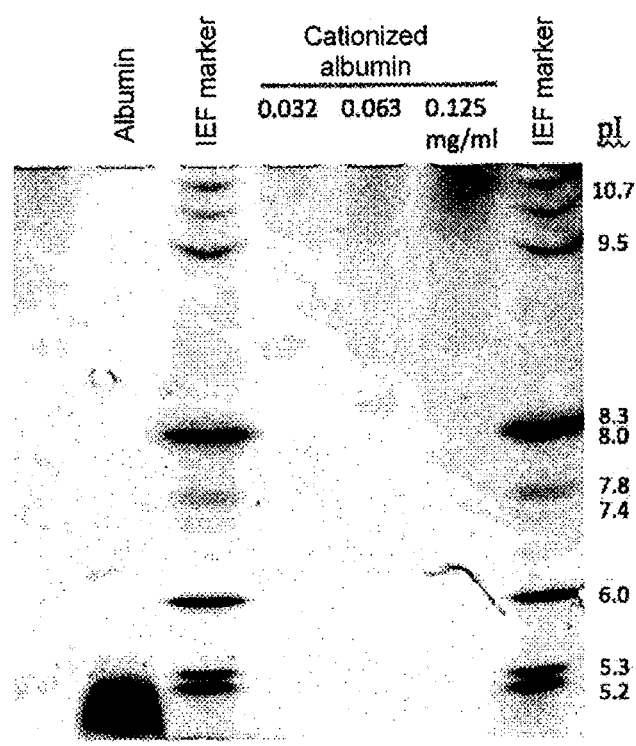
[Figure 2]
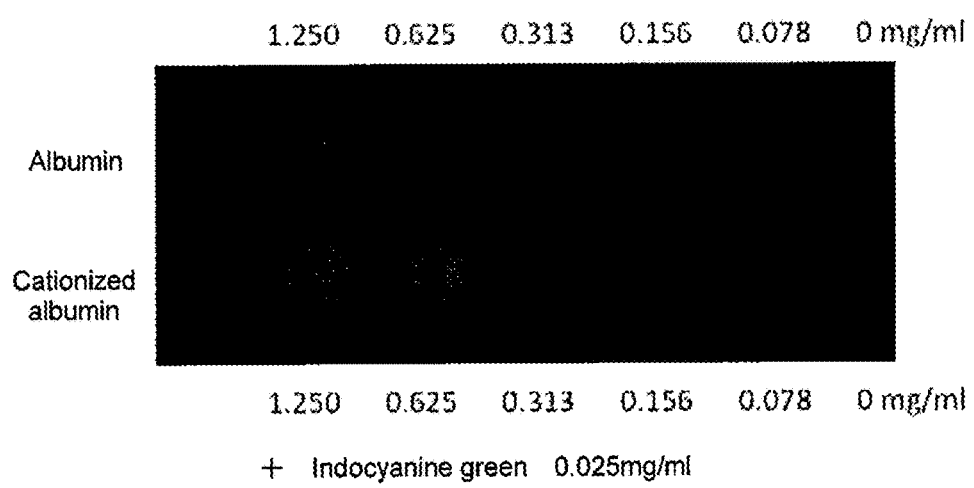

[Figure 3]
| | Cartilage damage model | Image taken by infrared camera |
|---|---|---|
| Control plot (intact) | 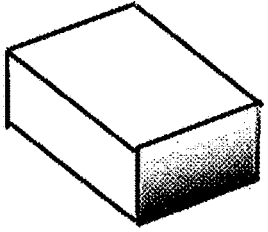 | 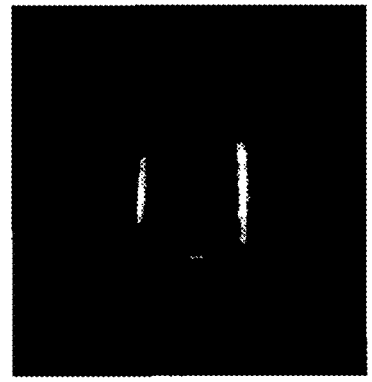 |
| Test plot 1 (half-surface defective) | 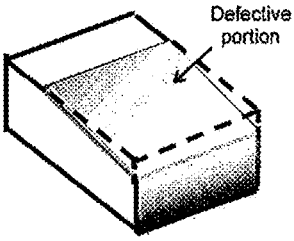 | 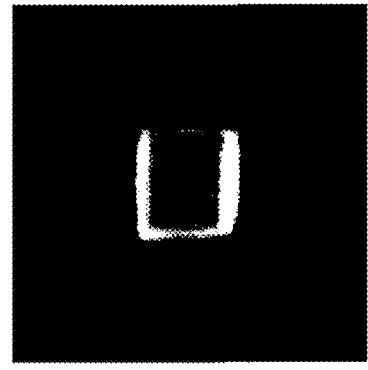 |
| Test plot 2 (center portion defective) | 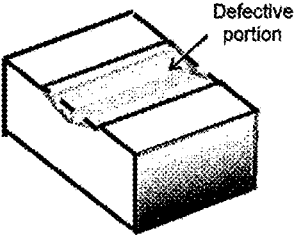 | 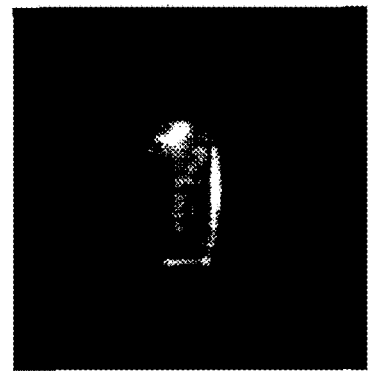 |

[Figure 4]
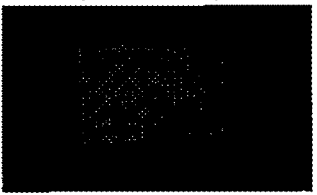

[Figure 5]
| Image under visible light | Image under near-infrared light | |
|---|---|---|
| Upper surface | Upper surface | Side surface |
| 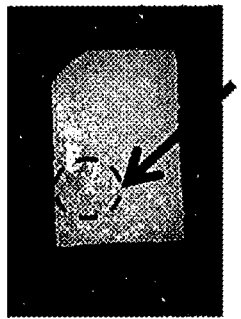 | 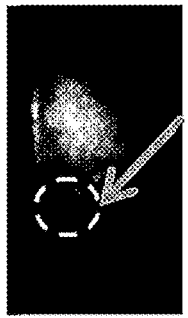 |  |

ARTICULAR CARTILAGE IMAGING COMPOSITION

TECHNICAL FIELD

The present invention relates to an articular cartilage imaging composition specifically adsorbing to a damaged site of articular cartilage, thereby visualizing the damaged site of articular cartilage.

BACKGROUND ART

Osteoarthritis (OA) is a joint disorder, which is presumably induced by degeneration in articular cartilage as a main cause and frequently observed in e.g., the knee, hip and femur joints. OA is caused by not only aging and overload but also sports injury and obesity. Particularly, the number of patients with knee osteoarthritis is estimated to be 25,300,000 in Japan (ROAD project, the 22nd Century Medical and Research Center, The University of Tokyo Hospital, 2009) and is twice or more larger in the United States than in Japan. Also, in densely populated areas such as China, India and African countries where e.g., working conditions and environmental conditions are considered to be severer than in Japan, the number of OA patients will increase from now on. At present, in Japan, 75,000 (Yano Research Institute Ltd., 2011) patients are reported to undergo total artificial knee joint replacement surgery as a final therapy. Artificial joint replacement per se is a highly invasive therapy. In addition, the mechanical life of the artificial joint is limited and depending on circumstances, the artificial joint must be repeatedly exchanged.

In order to prevent exacerbation of knee osteoarthritis and avoid ultimate artificial joint replacement surgery, it is important to receive an appropriate treatment early. For early treatment, early detection of cartilage degeneration is required; however, it is difficult to detect early-stage cartilage degeneration by a conventional X-ray imaging (roentgen photograph) and MRI scan. The presence or absence of cartilage degeneration also can be checked by observing cartilage by use of an arthroscope (a kind of endoscope); however, in this method, a doctor in charge touches the site of the cartilage surface layer by use of a tool such as forceps under an arthroscope and determines the presence or absence of cartilage degeneration based on a sense of touch. Because of this, early detection is mostly left in the experience and skill of the doctor. In addition, there is a problem that the border line between normal cartilage and degenerative cartilage cannot be clearly identified.

If there is a non-Invasive or less-invasive examination method that enables early detection of cartilage degeneration without depending upon the experience and skill of a doctor alone, the presence or absence and the progress of cartilage degeneration can be figured out and therapeutic strategy can be easily created. As the non-invasive or less-invasive examination method, a method using an in-vivo imaging technique for visualizing a living tissue is known. As the in-vivo imaging technique, various techniques are known, including positron emission tomography (PET), nuclear magnetic resonance imaging (MRI), ultrasonography (US) and photoacoustic imaging (PAI). Other than these, a fluorescence imaging technique such as fluorescent molecule tomography (FMT) is known, in which a fluorescent substance is focused on a site of interest in a living body and the site is captured highly sensitively. The fluorescence imaging technique has attracted attention because it can non-invasively visualize a site of interest in a site specific manner.

In order to apply the aforementioned in-vivo fluorescence imaging technique to articular cartilage, several techniques relating to an imaging probe specifically binding to an articular cartilage tissue and accumulating there have been proposed. In Patent Literature 1, a cartilage marker specifically binding to cartilage matrix is described, which is obtained by allowing a signal generation means, such as a fluorescent substance, to bind to a polyarginine peptide having 6 to 20 arginine residues or a polylysine peptide having 6 to 20 lysine residues. Further in Patent Literature 2, a cartilage tissue marker is described, which consists of a lysine oligomer derivative obtained by allowing a group capable of generating or absorbing an electromagnetic wave to bind to a lysine oligomer in which ε-amino group of lysine and a carboxyl group are connected via a peptide bond.

CITATION LIST

Patent Literature

[Patent Literature 1]
Japanese Patent Laid-Open No. 2009-023993
[Patent Literature 2]
International Publication No. WO 2013/137302

SUMMARY OF INVENTION

Technical Problem

Patent Literature 1 and Patent Literature 2 state that these cartilage markers specifically bind to normal articular cartilage; however, they are silent about how to act on abnormal cartilage, i.e., degenerative cartilage, such as osteoarthritis. To describe more specifically, at present, there is such a problem that there is no diagnostic articular cartilage imaging composition which can clearly distinguishably visualize a normal site and an abnormal site in articular cartilage.

In addition, as described above, it has been desired to develop an examination method that enables early detection of cartilage degeneration without requiring much experience and skill of a doctor.

The present invention has been conceived in consideration of the aforementioned circumstances. An object of the present invention is to provide an articular cartilage imaging composition which can clearly distinguishably visualize a normal site and an abnormal site in articular cartilage.

Another object of the present invention is to provide an articular cartilage imaging composition which facilitates early detection of cartilage degeneration and accurate identification of a degree of degeneration, thereby contributing to prompt determination of treatment strategy.

Solution to Problem

For attaining the aforementioned objects, the articular cartilage imaging composition of the present invention contains a positively charged molecule, which is labeled with a labeling molecule. Normal cartilage has a surface layer formed of a plurality of layers consisting of flat cells. On the other hand, degenerative cartilage has a state where a cell layer is removed and cartilage matrix rich in fiber and having an irregular tissue structure is exposed or a state where a defect is formed from the surface layer toward the deep site. The articular cartilage imaging composition of the present invention contains a positively charged molecule labeled with a labeling molecule. The positively charged molecule intensively penetrates exposed cartilage matrix and adsorbs thereto. Likewise, since the articular cartilage imaging composition of the present invention is adsorbed intensively to a degenerative site of cartilage, a normal site and a degenerative site of the articular cartilage can be distinguishably visualized.

The positively charged molecule of the articular cartilage imaging composition of the present invention is preferably a positively charged protein or peptide compound. As the positively charged molecule serving as a constituent of the articular cartilage imaging composition, a substance ubiquitously present in a living body, having high safety, and being easily handled and simply labeled with a labeling molecule is selected.

The protein or peptide compound of the articular cartilage imaging composition of the present invention is preferably an albumin, an albumin decomposition product or a modified albumin compound. Accordingly, a preferable substance as a protein or peptide compound constituting the positively charged molecule is selected.

The positively charged molecule of the articular cartilage imaging composition of the present invention is further preferably a positively charged compound having a sugar chain. As the positively charged molecule serving as a constituent of the articular cartilage imaging composition, a substance ubiquitously present in a living body, having high safety, and being easily handled and simply labeled with a labeling molecule is selected.

The compound having a sugar chain of the articular cartilage imaging composition of the present invention is preferably dextran, cyclodextrin or a derivative thereof. Accordingly, a preferable substance as a compound having a sugar chain constituting the positively charged molecule is selected.

The labeling molecule of the articular cartilage imaging composition of the present invention is preferably at least one substance selected from the group consisting of a fluorescent substance, a radioisotope, an X-ray absorbing substance, an antibody molecule and a molecule having a recognition site recognized by a specific antibody. Since each of the aforementioned positively charged molecules is labeled with a labeling molecule, the position of the positively charged molecule adsorbed to a degenerative cartilage site can be visualized by a fluorescent substance, a radioisotope, an X-ray absorbing substance, an antibody molecule or a molecule having a recognition site recognized by a specific antibody.

Of the aforementioned labeling molecules, the fluorescent substance is preferably indocyanine green. Accordingly, a labeling molecule having high safety, effectively visualizing and detecting a degenerative site can be selected.

The labeling molecule of the articular cartilage imaging composition of the present invention is preferably at least one substance selected from the group consisting of a magnetic particle, a metal particle, a metal nanoparticle and another nano-material containing substance. Accordingly, the position of positively charged molecule adsorbed to a cartilage degenerative site can be detected by e.g., X-ray CT, MRI, Raman spectroscopy or a plasmon resonance method.

Advantageous Effects of Invention

According to the present invention, it is possible to provide an articular cartilage imaging composition having the following excellent effects.

(1) A normal site and an abnormal site (degenerative site) in articular cartilage can be clearly distinguishably visualized.

(2) Cartilage degeneration can be early detected and a degree of degeneration can be easily and accurately identified.

(3) Diagnosis or treatment can be made by visualizing a degenerative site in articular cartilage in vivo by using an articular cartilage imaging composition in diagnosis or surgery under an arthroscope.

(4) A degenerative state of cartilage can be non-invasively or less invasively diagnosed using an in-vivo imaging technique, e.g., by injecting the articular cartilage imaging composition in a joint space.

(5) The articular cartilage imaging composition is easy to handle since it is constituted of highly safe substances. Also, decomposition products thereof are highly safe, too.

(6) After examination and surgery are completed, the articular cartilage imaging composition is efficiently removed through metabolism, hydrolysis or dilution with tissue fluid.

BRIEF DESCRIPTION OF DRAWINGS

FIG. 1 is a photograph showing the results of isoelectric point electrophoresis of a positively charged bovine serum albumin in Example 1.

FIG. 2 is a photograph showing fluorescent emission resulting from binding of a positively charged albumin or an albumin to indocyanine green in Example 2.

FIG. 3 is a photograph showing the imaging results of a cartilage damage model by the articular cartilage imaging composition of the present invention of Example 3.

FIG. 4 is a photograph showing the imaging results of a cartilage damage model and a cartilage intact model by the articular cartilage imaging composition of the present invention of Example 4.

FIG. 5 is a photograph showing the imaging results of a damaged cartilage of a human by the articular cartilage imaging composition of the present invention of Example 5.

DESCRIPTION OF EMBODIMENTS

The articular cartilage imaging composition of the present invention contains a labeled positively charged molecule. In the present invention, the "positively charged molecule" refers to a molecule having a positive charge (cationic charge) and capable of selectively adsorbing to degenerative cartilage.

Cartilage is classified into the connective tissue and constituted of cartilage matrix as an extracellular matrix, predominantly present and cartilage cells present like dots. The cartilage constituting a joint is called as hyaline cartilage. The major components of cartilage matrix of the hyaline cartilage are collagen and proteoglycan. The proteoglycan contains a side chain having a negative charge such as chondroitin sulfate, keratan sulfate and heparan sulfate and negatively charged in whole. Normal cartilage has a surface layer formed of a plurality of layers consisting of flat cells. On the other hand, degenerative cartilage has a state where a cell layer is removed and cartilage matrix rich in fiber and having an irregular tissue structure is exposed or a state where a defect is formed from the surface layer toward the deep site. The positively charged molecule contained in the articular cartilage imaging composition of the present invention is presumed to specifically adsorb to proteoglycan present in the cartilage matrix exposed after the surface layer of the cartilage tissue is removed.

The positively charged molecule in the present invention is not particularly limited as long as the molecule can selectively adsorb to degenerated cartilage; however, in view of safety and easiness of handling, a positively charged protein or peptide compound or a positively charged compound having a sugar chain is preferable. Note that, the "protein" herein includes a wide variety of proteins such as a glycoprotein, a lipoprotein and a nucleotide-binding protein.

As the protein or peptide compounds positively charged to be used as the positively charged molecule in the present invention, plasma proteins and various types of albumins are preferable, and particularly a serum albumin is preferable. The plasma proteins and various types of albumins include decomposition products and modified compounds of albumins. The positively charged albumin (cationized albumin) is specifically adsorbed to the cartilage matrix; however, it is less invasive to the cells within a cartilage tissue. Thus, the cationized albumin is not easily taken up by cells from the surface of the normal cartilage tissue and virtually not adsorbed to the cartilage matrix present within the surface of the normal cartilage tissue. Because of this, the cationized albumin is intensively adsorbed by a degenerative (abnormal) site of the articular cartilage tissue. In order to be intensively adsorbed by a cartilage damaged site, an albumin or a decomposed/modified compound of an albumin is preferably charged so as to satisfy an isoelectric point (pI) of 8 or more and particularly preferably 10 or more. The safety of the articular cartilage imaging composition to be applied to a living body can be further enhanced by selecting an albumin which is less invasive to the cells within a cartilage tissue, as described above. Furthermore, if an albumin molecule having a large molecular weight is selected, the number of labels (labeling molecules) can be increased. For the reason, if e.g., a fluorescent substance is used as a labeling molecule, brightness can be improved. Since such a control can be made, detection based on a labeling molecule, in other words, visualization, can be easily made.

As the compound having a sugar chain to be positively charged in the same manner as in the aforementioned albumin and used as the positively charged molecule of the present invention, a linear or cyclic compound having a sugar chain is preferable. As the linear compound having a sugar chain, dextran or a dextran derivative is particularly preferable. As the cyclic compound having a sugar chain, cyclodextrin or a cyclodextrin derivative is particularly preferable. These positively charged compounds, I.e., dextran, cyclodextrin and a derivative thereof, are specifically adsorbed to the cartilage matrix similarly to the aforementioned albumin; however, they are less invasive to the cells within a cartilage tissue. Thus, the cationized dextran and cyclodextrin are not easily taken up by cells from the surface of the normal cartilage tissue and are virtually not adsorbed to the cartilage matrix present in the surface layer of the normal cartilage tissue. Because of this, cationized dextran or cyclodextrin is adsorbed to a degenerative (abnormal) site of the articular cartilage tissue. In order not to make an invasion upon cells of the cartilage tissue, dextran or cyclodextrin preferably has a molecular weight of 3,000 or more and more preferably 10,000 or more. The safety of the articular cartilage imaging composition to be applied to a living body can be further improved by selecting dextran or cyclodextrin less invasive to the cells within a cartilage tissue, as described above. If dextran or cyclodextrin having a large molecular weight is selected, the number of the labeling molecules can be increased. For the reason, if e.g., a fluorescent substance is used as a labeling molecule, brightness can be improved. Since such a control can be made, detection based on a labeling molecule, in other words, visualization, can be easily made. In addition, in the case of cyclodextrin, since a labeling molecule can be easily enclosed in the interior cavity of the molecule, the articular cartilage imaging composition of the present invention can be easily obtained.

Note that, in the present invention, the "articular cartilage imaging" refers to visualizing the state of articular cartilage, in other words, bringing the state of articular cartilage seen with the naked eye or through e.g., a device, with the help of a means such as images, numerical values or vectors. Visualization includes both visualization (for detection) of a sample taken from an articular cartilage tissue and in-vivo (in situ) visualization (for detection) of an articular cartilage tissue. Examples of the in-vivo visualization include visualization for common surgery, visualization for less-invasive examination or surgery using an arthroscope and visualization for less-invasive examination performed by injecting the composition of the present invention in a joint space by means of e.g., a syringe.

In the present invention, the labeling molecule refers to a molecule that directly or indirectly binds to a positively charged molecule or is enclosed by a positively charged molecule, thereby marking up the positively charged molecule and allowing detection of the presence of the positively charged molecule with the naked eye or through e.g., a device. As the labeling molecule, which is not particularly limited, e.g., a fluorescent substance, a radioisotope, a luminescent substance, an enzyme, an X-ray absorbing substance, an antibody molecule, a molecule (antibody recognition molecule) having a recognition site recognized by a specific antibody, a magnetic particle, a metal particle or a metal nanoparticle coated with glass can be appropriately used.

As an embodiment of the present invention, a fluorescent substance is preferably used as the labeling molecule because it is easily visualized or detected. As the fluorescent dye, e.g., indocyanine green, Alexa Fluor (registered trade mark) 488, Alexa Fluor 546, Alexa Fluor 555, Alexa Fluor 568, Alexa Fluor 594, Alexa Fluor 647, BODIPY (registered trade mark) FL, Texas Red (registered trade mark), Oregon Green (registered trade mark) 488, rhodamine B, rhodamine green, tetramethyl rhodamine, fluorescein, fluorescein isothiocyanate, phycoerythrin, phycocyanin, Cy3, Cy5, Cy7, are preferably used. Of them, indocyanine green is particularly preferably used, for the reason that it is highly safe and easily visualized or detected. Indocyanine green, which is irradiated with near-infrared light in the predetermined conditions, emits fluorescence falling within the near-infrared region and having a longer wavelength than the near-infrared light applied. The emission light cannot be virtually recognized directly with the naked eye. For observation, a device for detecting infrared light is required; however, since observation can be made in a dark field, the contrast tuning can be easily controlled when observation is made by an arthroscope, facilitating detection. These fluorescent molecules are used for labeling a positively charged molecule by an avidin-biotin binding method, inclusion or other methods known in the art.

When an antibody recognition molecule is used as a labeling molecule, fluorescence can be observed by use of not only the avidin-biotin method but also various types of fluorescent antibody reactions. When luciferin is used as a labeling molecule, light emission using a luciferin-luciferase reaction can be observed. As a labeling molecule, e.g., an X-ray absorbing substance, a magnetic nanoparticle and a metal nanoparticle can be used. If these are used as a labeling molecule, observation can be made by X-ray CT, MRI, Raman spectroscopy or a plasmon resonance method. Note that, in addition of detection by the aforementioned labeling molecule, infrared light absorption of hemoglobin abundantly present under the cartilage tissue and self-luminous phenomenon of a collagen fiber can be non-Invasively evaluated. Also, viscoelasticity of the tissue relative to shear stress by MR elastography (MRE) can be non-invasively evaluated.

The articular cartilage imaging composition of the present invention can further contain components other than the aforementioned molecules. Examples of the components (additives) include an isotonic agent, a buffer, a preservative and an antioxidant. As the isotonic agent, e.g., sodium chloride, glycerin, D-mannitol, D-sorbitol or glucose is preferably used. As the buffer, e.g., a phosphate buffer, an acetate buffer, a carbonate buffer and a citrate buffer are mentioned.

The articular cartilage imaging composition of the present invention can contain, other than the aforementioned additives, a substance for further preventing invasion of a positively charged molecule into the cartilage tissue. As such a material, for example, collagen and an albumin not positively charged or a derivative and decomposition product thereof, are mentioned.

Note that the articular cartilage imaging composition of the present invention can be used in a drug delivery system selectively binding to a cartilage damaged site, by binding a therapeutic agent having a damaged cartilage repair action or a scaffold molecule such as type I collagen serving as a scaffold for e.g., a cell sheet for regenerative medicine and cell therapy in place of the aforementioned labeling molecule, and also used in postoperative management after scaffold transplantation.

Now, a method for using the articular cartilage imaging composition of the present invention will be described. The articular cartilage imaging composition of the present invention is preferably a liquid preparation because a liquid can be easily applied. When the composition of the present invention is applied within a living body, it can be applied to an articular cartilage surface layer by spraying, dropping or coating under an arthroscope or injection into a joint space. In the case of application under an arthroscope, it is preferable that a cartilage surface is washed with e.g., Ringer's lactate or physiological saline to remove mucosal fluid (synovial fluid) in a joint space, and thereafter, the articular cartilage imaging composition of the present invention is applied such as spaying or coating. After the articular cartilage imaging composition is applied by e.g., spraying, the articular cartilage imaging composition is allowed to stand still for a predetermined time for penetration. The predetermined time herein is specifically, preferably about 3 minutes to 30 minutes, more preferably about 5 minutes to 20 minutes and further preferably about 10 minutes to 15 minutes, in view of permeability to a target tissue. Thereafter, the articular cartilage is rinsed with e.g., Ringer's lactate to remove nonspecific adsorption and excessive articular cartilage imaging composition. After that, e.g., fluorescence of a labeling molecule is detected.

As the detection method using a labeling molecule, which is not particularly limited, a method in which a labeling molecule is measured by inserting an arthroscope and an optical fiber having a filter which controls excitation light to be suitable for the labeling molecule. For example, when a fluorescent indicator, indocyanine green, is used as a labeling molecule, green fluorescence (peak wavelength: 800 to 850 nm) of indocyanine green can be easily observed by images of a CCD camera through an appropriate filter. In imaging the detection result, e.g., fluorescence intensity can be converted into e.g., color and numerical values desired by the operator by use of appropriate software, and displayed. In addition, in a visible image of a cartilage degenerative site visualized by the articular cartilage imaging composition, as mentioned above, if e.g., the contrasting density and color change are identified or detected, the roughness of the degenerative cartilage tissue surface, more specifically, the degeneration level of the cartilage can be detected. Since the time required for diagnosis or surgery using the arthroscope is usually as short as 1 to 3 hours, it is sufficient that the working time of the articular cartilage imaging composition is similarly about 1 to 3 hours. After completion of diagnosis or surgery, washing with e.g., Ringer's lactate or physiological saline is performed a plurality of times. In this manner, the composition is almost discharged (removed). The residue if remains can be decomposed by e.g., hydrolysis and discharged (removed).

When the articular cartilage imaging composition of the present invention is applied to a normal cartilage tissue, the positively charged molecule therein is rejected by a shell-like structure formed of lamellar cells and cannot make an invasion upon cartilage cells. As a result, the normal cartilage tissue is not visualized. In contrast, in the case of degenerative cartilage tissue having no lamellar-cell layer, the articular cartilage imaging composition is adsorbed to the exposed cartilage matrix oriented manner. As a result, the degenerative cartilage tissue is highlighted. In a conventional detection method, it was difficult to detect and identify the early stage of cartilage degeneration, in other words, "cartilage degeneration grade 1" where lamellar-cell layer is just removed. However, the articular cartilage imaging composition of the present invention makes it possible to identify and detect "cartilage degeneration grade 1" and enables prompt therapy of patients.

The articular cartilage imaging composition of the present invention makes it possible to figure out the state of damage in the tissue (cartilage, cruciate ligament and meniscus) within the joint by use of an arthroscope and treat the damage, with the result that less invasive diagnosis and treatment can be made. Up to now, an image of the articular cartilage displayed on a monitor by an arthroscope under visible light looks white and a brightness level is high. For this reason, it was difficult to determine degeneration and damage of a cartilage surface layer. However, degeneration and defective sites on a cartilage surface can be labeled by use of the composition of the present invention, with the result that the state of a cartilage damage, which is rarely observed under visible light, can be observed by allowing a labeling molecule to emit infrared fluorescence in a dark field.

Now, Examples of the present invention will be described below; however, the present invention is not limited to these Examples.

EXAMPLES

Example 1

1. Preparation of Positively Charged Albumin

A bovine serum albumin (product manufactured by Sigma-Aldrich Co. LLC.) (5 g) was dissolved in pure water (25 mL). Separately, anhydrous ethylenediamine (67 mL)

(product manufactured by Sigma-Aldrich Co. LLC.) was added in pure water (500 mL). To this, 6N hydrochloric acid (about 350 mL) was gradually added to adjust pH to 4.75 in ice water. To the resultant ethylenediamine solution, 1-ethyl-3-(3-dimethylaminopropyl)carbodiimide hydrochloride (1.8 g) (product manufactured by Sigma-Aldrich Co. LLC.) was added and the aqueous bovine serum albumin solution prepared above was added. The mixture was stirred for 2 hours while the preparation container was cooled in ice water to control the temperature and pH of the mixture. The reaction was terminated by adding a 4 M acetate buffer (5 mL). The resultant solution was dialyzed against pure water at 4° C. for 72 hours and then lyophilized. The crystal obtained by lyophilization was white and glossy and had thin film-like appearance.

The lyophilized product prepared as mentioned above and the bovine serum albumin used as a raw material were subjected to measurement of isoelectric points to check whether or not a positively charged albumin was obtained. The lyophilized product and bovine serum albumin were each dissolved in pure water, and applied to Novex (registered trade mark) IEF gel (product manufactured by Life Technologies Corporation) and subjected to isoelectric point electrophoresis. The results are shown in FIG. 1. As is shown in FIG. 1, the pI of a bovine serum albumin is usually about 4.9; however, the pI of the lyophilized product was as high as about 11. From this, it was found that the lyophilized product was highly cationized. From this, it was confirmed that positively charged albumin was obtained.

Example 2

2. Investigation on Optimal Concentration of Positively Charged Albumin and Indocyanine Green A fluorescent dye, indocyanine green (ICG), emits no fluorescence in the state of an aqueous solution (containing ICG alone); however, ICG emits fluorescence within a near-infrared region when it binds to a protein. ICG was allowed to bind to the positively charged albumin prepared in Example 1 and the intensity of fluorescence emitted from ICG was measured as follows. Note that, the intensity of fluorescence emitted from ICG when an albumin not positively charged, serving as a control, bound thereto was measured.

The positively charged albumin prepared in Example 1 was dissolved in pure water to prepare solutions having a concentration of 1.250 mg/mL, 0.625 mg/mL, 0.313 mg/mL, 0.156 mg/mL and 0.078 mg/mL. Separately, indocyanine green (product manufactured by Sigma-Aldrich Co. LLC.) was dissolved in pure water to prepare a 0.025 mg/mL solution. An aliquot (50 µL) was taken from each of the positively charged albumin solutions different in concentration and the ICG solution, added to each well of a 96-well ELISA plate and mixed. Infrared fluorescence emitted from the resultant solution was taken by an infrared observation camera system (pde-neo C10935-20, manufactured by Hamamatsu Photonics K. K.) (excitation light: 760 nm, fluorescence 830 nm). A control was prepared in the same manner as above except that bovine serum albumin (product manufactured by Sigma-Aldrich Co. LLC.) was used in place of the positively charged albumin, and subjected to the same test. The results are shown in FIG. 2.

As is shown in the photograph of FIG. 2, fluorescence from the albumin not positively charged was able to be identified in experimental plots having an albumin concentration of 0.313 mg/mL (albumin concentration; 0.156 mg/mL, ICG concentration; 0.0125 mg/mL) or more with the naked eye. In contrast, fluorescence from the positively charged albumin was able to be identified in experimental plots having an albumin concentration of 0.156 mg/mL (positively charged albumin concentration; 0.078 mg/mL, ICG concentration; 0.0125 mg/mL) or more with the naked eye. From this, it was found that fluorescence can be identified in the positively charged albumin, which was lower in concentration than an albumin generally used. Note that, when a test was carried out by adding ICG at a higher concentration than the aforementioned test concentration (0.0125 mg/mL), it was confirmed that the brightness of fluorescence increases.

Example 3

3. Imaging (1) of Cartilage Damage Model Using Bovine Normal Articular Cartilage by Articular Cartilage Imaging Composition Articular cartilage of the forelimb shoulder of a cattle (2 to 3 weeks old) was excised out and cut into pieces of about 1.5 cm×about 2 cm in size and subchondral bone was removed. Subsequently, as shown in the illustration of a cartilage damage model of FIG. 3, the surfaces of the articular cartilage pieces excised out were partly sliced by a razor at a depth of about 0.1 to 0.2 mm to make a defect in the cartilage surface. In consideration of use in actual clinical sites, each of the articular cartilage pieces was washed by spraying saline (about 5 ml) by a syringe. Then, 200 µl of the articular cartilage imaging composition (positively charged albumin concentration: 2.5 mg/mL, ICG concentration: 0.125 mg/m L) prepared by dissolving a positively charged albumin and ICG in pure water, was added dropwise on the surface of a hydrophobic plastic plate and the articular cartilage piece was placed face down on the surface of the hydrophobic plastic plate to dip the piece in the articular cartilage imaging composition. About 10 to 15 minutes later, excessive articular cartilage imaging composition was washed away with saline. Images of individual articular cartilage pieces were taken by an infrared camera (product manufactured by Hamamatsu Photonics K. K.) and recorded.

The images observed by an infrared camera are shown in FIG. 3. In the articular cartilage piece (surface is not excised out) of the control plot, penetration and adsorption of the articular cartilage imaging composition from the surface of the cartilage were not confirmed. Emission like a white line was observed; however, it was derived from attachment of the excessive articular cartilage imaging composition by capillary action to the outer peripheral side-surface of the articular cartilage piece. In contrast, in experimental plot 1 (a half portion of one of the cartilage surfaces was excised out by a razor to make a defect), emission of light derived from the articular cartilage imaging composition, which penetrated through the defect in the surface and adsorbed, was confirmed. Note that, emission like a white line was observed; however, it was derived from excessive articular cartilage imaging composition adsorbed by capillary action to the outer peripheral side-surface of the articular cartilage piece. In experimental plot 2 (a center portion of one of the cartilage surfaces by a razor), emission of light derived from the articular cartilage imaging composition, which penetrated from the defect potion of the center surface and adsorbed was confirmed. As described above, it was demonstrated that in the excised surface, the articular cartilage imaging composition of the present invention penetrates to the depth, adsorbs thereto and emits intensive fluorescence.

Example 4

4. Imaging (2) of Cartilage Damage Model Using Bovine Normal Articular Cartilage by Articular Cartilage Imaging Composition Articular cartilage of the forelimb shoulder of a cattle (2 to 3 weeks old) was aseptically excised out and cut into pieces of about 1 cm×about 1.5 cm in size and subchondral bone was removed as much as possible. The cartilages excised out each were dipped in a physiological phosphate buffer. Subsequently, almost half (the right half as viewed from the top) of the surface of each of the articular cartilage pieces was cut by a scalpel (No. 11) to a depth of about 0.1 to 0.2 mm to form a defect in the cartilage surface. Owing to the treatment, the left half (as viewed from the top) of the articular cartilage piece remains intact and used as a control plot; whereas the right half (as viewed from the top) is used as a cartilage surface damage model. In order to confirm the position in measurement and observation, one of the corners of the damaged surface was diagonally cut off. In prior to fluorescence observation, a physiological phosphate buffer (about 2 to 3 mL) was sprayed to each of the articular cartilage pieces by a syringe and washed. Excessive buffer was removed with Kimwipe (registered trade mark). Then, the following sample solutions 1 to 4 (50 µL for each) were added dropwise to respective hydrophobic petri dishes and the articular cartilage piece was placed face down on the sample solution added dropwise on the surface of the hydrophobic petri dish to impregnate the surface of the articular cartilage piece with the sample solution. About 10 minutes later, excessive sample solution was washed away with a physiological phosphate buffer and excessive buffer was removed by Kimwipe. Each of the articular cartilage pieces was placed on a piece of black paper and photographed under near-infrared light and visible light.

Sample solutions 1 to 4 used in this example were prepared by separately dissolving individual components in pure water. Sample solution 1 contained pure water alone; Sample solution 2 contained ICG in a concentration of 0.125 mg/mL; Sample solution 3 contained an albumin in a concentration of 2.5 mg/mL and ICG in a concentration 0.125 mg/mL; and Sample solution 4 contained a positively charged albumin in a concentration 2.5 mg/mL and ICG in a concentration of 0.125 mg/mL. In shooting under near-infrared light, each of the sample solutions of the articular cartilage pieces was excited by a light source (excitation wavelength: 770 nm, 30 mA for each), which was prepared by arranging 16 near-infrared light-emitting diodes in the form of a circle, and images were taken by high sensitive CCD camera (ORCA-ER, manufactured by Hamamatsu Photonics K. K.) via a filter for ICG (832 nm) (BrightLine ICG-B, manufactured by Semrock) all in the same conditions (100 ms, low light and 8×binning mode). After shooting under near-Infrared light, monochrome shooting was performed under visible light.

The results are shown in FIG. 4. In each of the photographs taken in visible light and near-infrared light, the left half shows an intact control and the right half shows a damage model. In the case of Sample solution 1 (pure water alone), it was confirmed that light is not emitted from both surfaces. However, in Sample solution 2 (ICG alone), fluorescence was emitted from the intact control. Fluorescence is conceivably derived from ICG adsorbed to a protein in the cartilage surface. In contrast, no fluorescence was observed in the damage model. This was considered that when the surface of cartilage is damaged, sugar chain such as glycosaminoglycan is exposed in the cartilage surface in a larger amount than proteins and thus ICG is not adsorbed to these sugar chains. In contrast, Sample solution 3 (albumin+ICG), extremely weak fluorescence was emitted from both surfaces; however, there was no difference in emission intensity between them. From this, it was found that an albumin has virtually no adsorption specificity to cartilage matrix and a cell layer, and considered that albumin contained in a sample solution binds to ICG and thus ICG loses adsorption activity to proteins on the cartilage surface. In the case of Sample solution 4 (positively charged albumin+ICG), it was observed that intensive fluorescence was emitted from the damage surface. This was presumed that a positively charged albumin penetrated thorough a damaged surface into the interior and adsorbed to a cartilage intermediate layer containing a large amount of negative charge. In the intact control surface, cell layers are densely arranged and the amount of negative charge is low. From this, it was considered that the amount of positively charged albumin adsorbed is low. ICG was saturated with proteins due to inclusion by a positively charged albumin and conceivably not newly adsorbed to proteins in the cartilage surface. As described above, it was demonstrated that the articular cartilage imaging composition of the present invention constituted of a positively charged albumin and ICG, penetrates the cartilage damaged portion, adsorbs and emits fluorescence more intensively than a normal cartilage surface portion to visualize the damaged portion.

Example 5

5. Imaging of Human Damaged Cartilage with Articular Cartilage Imaging Composition Imaging of a human articular cartilage damaged portion with the articular cartilage imaging composition of the present invention was performed. As a test material, degenerative cartilage of human arthritis, which was medical waste excised for artificial knee joint surgery, was used. The articular cartilage was aseptically excised out and cut into pieces of about 1 cm×about 1.5 cm in size. The cartilage excised out was dipped in a physiological phosphate buffer. Prior to fluorescent observation, a physiological phosphate buffer (about 2 to 3 mL) was sprayed to the articular cartilage pieces by a syringe and washed and then color photographs were taken under visible light. Excessive buffer was removed with Kimwipe (registered trade mark). Then, 100 µL of an articular cartilage imaging composition (positively charged albumin concentration: 2.5 mg/mL, ICG concentration: 0.125 mg/mL) prepared by dissolving a positively charged albumin and ICG in pure water was placed on a hydrophobic petri dish and the articular cartilage piece was placed face down on the petri dish to impregnate the surface of the articular cartilage piece with the articular cartilage imaging composition. About 10 minutes later, excessive imaging composition was washed away with a physiological phosphate buffer (2 to 3 mL) and excessive buffer was removed by Kimwipe. Each of the articular cartilage pieces was placed on a piece of black paper, and the upper surface and side surface were photographed under near-infrared light. In shooting under near-infrared light, the sample solution in each of the articular cartilage pieces was excited by a light source (excitation wavelength: 770 nm, 30 mA for each), which was prepared by arranging 16 near-infrared light-emitting diodes in the form of a circle, and images were taken by a high sensitive CCD camera (ORCA-ER, manufactured by Hamamatsu Photonics K. K.) via a filter for ICG (832 nm) (BrightLine ICG-B, manufactured by Semrock) all in the same conditions (100 ms, low light and 8×binning mode, Auto-contrast mode).

The results are shown in FIG. 5. Since the human degenerative cartilage used in the example had a severe osteoarthritis, intensive fluorescence was emitted from almost all of the articular cartilage pieces. From this, it was found that in the composition containing a positively charged albumin and ICG, the positively charged albumin suppresses non-specific adsorption of ICG to a biological protein, preferentially adsorbs to negative charge abundantly present in the cartilage intermediate layer and emits fluorescence. Note that, as shown in FIG. 5, it was found that fluorescence emitted from a thin red portion of a cartilage piece surface and confirmed when observation is made under visible light is low in intensity compared to the peripheral portion thereof. Since the thin red portion is a tissue close of the edge of articular cartilage, the portion was considered to be a tissue containing blood vessel like a synovial tissue formed on the cartilage surface and the synovial tissue presumably delayed penetration of the imaging composition of the present invention.

INDUSTRIAL APPLICABILITY

The articular cartilage imaging composition of the present invention enables early detection of degeneration of cartilage, which is a trigger cause of knee osteoarthritis and definite identification of the border between normal cartilage and degenerating cartilage. The articular cartilage imaging composition of the present invention cannot only visualize a degenerative site in articular cartilage in vivo for e.g., diagnosis or surgery under an arthroscope but also non-invasively or less invasively visualize the degenerative state of cartilage by injecting the articular cartilage imaging composition of the present invention in a joint space and the degenerative state can be observed by using an in-vivo imaging technique. Furthermore, the articular cartilage imaging composition of the present invention is useful in evaluating, a degree of cartilage damage and a degree of improvement, and in drug discovery research and pathological research on articular cartilage diseases in excised articular cartilage tissues or regenerated articular cartilage tissues.

The invention claimed is:

1. A method for visualizing a degenerative site of articular cartilage, comprising a step of spraying, adding dropwise, applying or dipping an articular cartilage imaging composition containing a positively charged albumin labeled with indocyanine green to a surface of articular cartilage having a degenerative site, thereby absorbing the positively charged albumin to the degenerative site of the articular cartilage; a step of washing the articular cartilage to remove excessive articular cartilage imaging composition; and a step of detecting indocyanine green of the positively charged albumin absorbed to the degenerative site of the articular cartilage.

2. The method for visualizing a degenerative site of articular cartilage according to claim 1, wherein the degenerative site of the articular cartilage is a state where a lamellar cell layer of a cartilage tissue is removed or a state where a defective portion is present from the surface layer toward the deep portion of a cartilage tissue.

* * * * *